US009757427B2

(12) United States Patent
Hu et al.

(10) Patent No.: US 9,757,427 B2
(45) Date of Patent: Sep. 12, 2017

(54) COMBINATION COMPRISING ZIDOVUDINE AND POLYMYXIN

(71) Applicant: HELPERBY THERAPEUTICS LIMITED, London (GB)

(72) Inventors: Yanmin Hu, London (GB); Anthony Coates, London (GB)

(73) Assignee: HELPERBY THERAPEUTICS LIMITED, London (GB)

( * ) Notice: Subject to any disclaimer, the term of this patent is extended or adjusted under 35 U.S.C. 154(b) by 0 days.

(21) Appl. No.: 14/772,538

(22) PCT Filed: Mar. 20, 2014

(86) PCT No.: PCT/GB2014/050878
§ 371 (c)(1),
(2) Date: Sep. 3, 2015

(87) PCT Pub. No.: WO2014/147405
PCT Pub. Date: Sep. 25, 2014

(65) Prior Publication Data

US 2016/0030506 A1 Feb. 4, 2016

(30) Foreign Application Priority Data

Mar. 22, 2013 (GB) .................................. 1305277.4

(51) Int. Cl.
*A61K 31/7072* (2006.01)
*A61K 38/12* (2006.01)

(52) U.S. Cl.
CPC .......... *A61K 38/12* (2013.01); *A61K 31/7072* (2013.01)

(58) Field of Classification Search
CPC ............................ A61K 38/12; A61K 31/7072
See application file for complete search history.

(56) References Cited

U.S. PATENT DOCUMENTS 4,245,742 A * 1/1981 Rossmo .................... A61J 7/04 206/533

OTHER PUBLICATIONS

Pournaras et al., Activity of tigecycline alone and in combination with colistin and meropenem against Klebsiella pneumoniae carbapenemase (KPC)-producing Enterobacteriaciae strains by time-kill assay, Int. J. Antimicrob. Agents, 37 (2011) 244-247.*

Chaudhari and Patil, Pharmaceutical Excipients: A Review, Int. J. Adv. Pharm., vol. 1(1), Jan.-Mar. 2012, pp. 21-34.*

Rita Murri et al., "Prolonged Efficiency of Secondary Prophylaxis with Colistin Aerosols for Respiratory Infection Due to Pseudomonas aeruginosa in Patients Infected with Human Immunodeficiency Virus", Clinical Infectious Diseases, Jan. 1, 1996, pp. 641-643, vol. 23, <http://cid.oxfordjournals.org/content/ 23/3/641.full.pdf>.

Polly E. Kintzel et al., "Otic Administration of Amphotericin B 0.25% in Sterile Water", The Annals of Pharmacotherapy, Mar. 1994, pp. 333-335, vol. 28, No. 3.

A. Doleans-Jordheim et al., "Zidovudine (AZT) has a bactericidal effect on enterobacteria and induces genetic modifications in resistant strains", European Journal of Clinical Microbiology & Infectious Diseases, Apr. 15, 2011, pp. 1249-1256, vol. 30, No. 10.

Takashi Saito et al., "Successful treatment with intravenous colistin for sinusitis, orbital cellulites, and pneumonia caused by multidrug-resistant metallo-beta-lactamase-producing *Pseudomonas aeruginosa* in a patient with acute myeloid leukemia", International Journal of Hematology, Mar. 24, 2009, pp. 689-692, vol. 89, No. 5.

Matthew E. Falagas et al., "Re-emergence of colistin in today's world of multidrug-resistant organisms: personal perspectives", Expert Opin. Investig. Drugs, Jan. 1, 2008, pp. 973-981, vol. 7, No. 17, <http://informahealthcare.com/doi/pdfplus/10.1517/13543784.17.7.973>.

International Search Report for PCT/GB2014/050878 dated Jun. 30, 2014.

International Preliminary Report on Patentability dated Oct. 1, 2015 issued by the International Bureau in counterpart International Application No. PCT/GB2014/050878.

* cited by examiner

*Primary Examiner* — Lianko Garyu
*Assistant Examiner* — Joseph Fischer
(74) *Attorney, Agent, or Firm* — Sughrue Mion, PLLC

(57) ABSTRACT

The present invention relates to the use of a combination of an anti-retroviral agent such as zidovudine and an anti-microbial agent for killing clinically latent microorganisms associated with microbial infections and to novel combinations comprising an anti-retroviral agent such as zidovudine and an anti-microbial agent for the treatment of microbial infections.

6 Claims, 2 Drawing Sheets

HT0120663

Colistin

| μg/ml | 8 | 4 | 2 | 1 | 0.5 | 0.25 | 0.125 | 0.0625 | 0.03125 | 0 |
|---|---|---|---|---|---|---|---|---|---|---|
| 8 | 0.37 | 0.37 | 0.37 | 0.37 | 0.37 | 0.37 | 0.37 | 0.37 | 0.37 | 0.37 |
| 4 | 0.37 | 0.36 | 0.37 | 0.37 | 0.37 | 0.37 | 0.37 | 0.37 | 0.37 | 0.37 |
| 2 | 0.37 | 0.37 | 0.38 | 0.37 | 0.42 | 0.61 | 0.62 | 0.65 | 0.98 | 0.57 |
| 1 | 0.38 | 0.37 | 0.38 | 0.37 | 0.59 | 0.58 | 0.66 | 0.77 | 0.79 | 1.20 |
| 0.5 | 0.38 | 0.37 | 0.38 | 0.37 | 0.62 | 0.60 | 0.71 | 0.80 | 0.85 | 1.15 |
| 0.25 | 0.38 | 0.37 | 0.38 | 0.40 | 0.43 | 0.60 | 0.72 | 0.81 | 0.84 | 1.11 |
| 0.125 | 0.37 | 0.37 | 0.41 | 0.71 | 0.50 | 0.65 | 0.72 | 0.76 | 0.83 | 1.14 |
| 0 | 0.38 | 0.38 | 0.63 | 0.78 | 0.64 | 0.60 | 0.70 | 0.83 | 0.89 | 1.15 |

Figure 2

COMBINATION COMPRISING ZIDOVUDINE AND POLYMYXIN

CROSS REFERENCE TO RELATED APPLICATIONS

This application is a National Stage of International Application No. PCT/GB2014/050878 filed Mar. 20, 2014, claiming priority based on British Patent Application No. 1305277.4 filed Mar. 22, 2013, the contents of all of which are incorporated herein by reference in their entirety.

Field of the Invention

The present invention relates to the use of an anti-retroviral agent in combination with an anti-microbial agent for treating microbial infections, particularly by killing clinically latent microorganisms associated with microbial infections.

Background of the Invention

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery,* 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet,* 357, 1179 (2001) and *Lancet,* 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science,* 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.,* 4, 395-404 (1988); *J. Med. Microbiol.,* 38, 197-202 (1993); *J. Bacteriol.,* 182, 1794-1801 (2000); ibid. 182, 6358-6365 (2000); ibid. 183, 6746-6751 (2001); *FEMS Microbiol. Lett.,* 202, 59-65 (2001); and *Trends in Microbiology,* 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad. Sci. USA*, 92, 11736-11740 (1995); *J. Bacteriol.*, 179, 6688-6691 (1997); and *Antimicrob. Agents Chemother.*, 44, 1771-1777 (2000)).

Brief Description of the Drawings

FIG. 2 shows HT0120663 in combination with Colistin against log phase *Escherichia coli* using chequerboard method.

Detailed Description of the Invention

Figure 1:
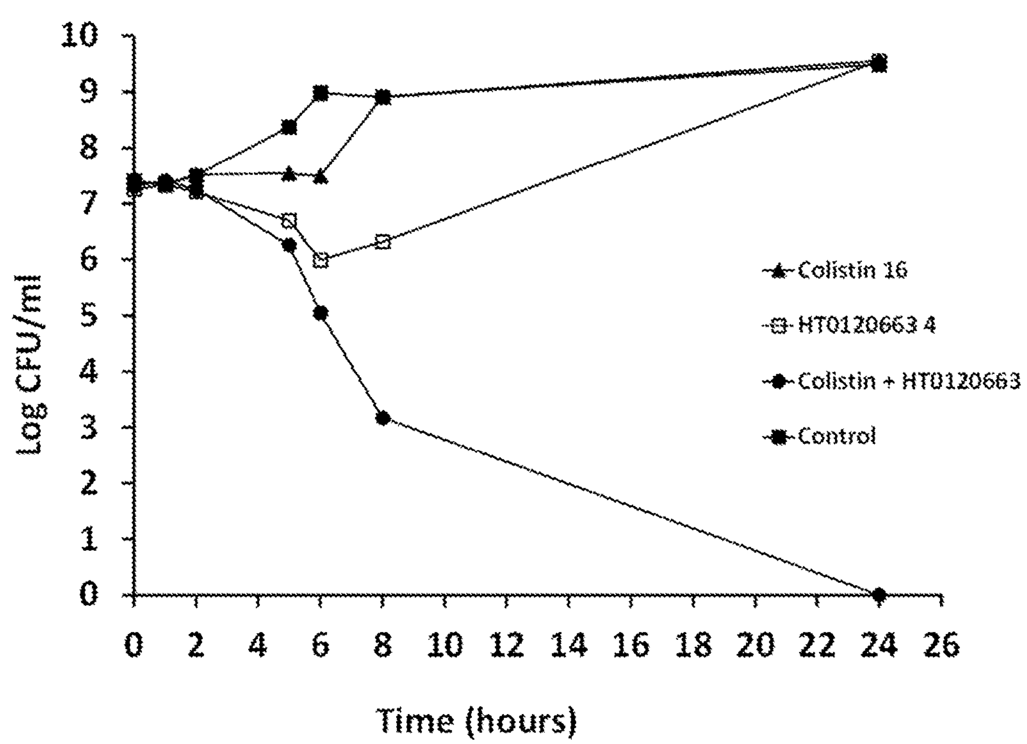
FIG. 1 shows HT0120663 in combination with Colistin against log phase *Klebsiella* using time kill curve.

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

Recently, there has been report of an anti-retroviral drug, zidovudine being active as an anti-microbial when combined with gentamicin. Thus, Doléans-Jordheim A. et al., disclosed (Eur J Clin Microbiol Infect Dis. 2011 October; 30(10):1249-56) that Zidovudine (AZT) had a bactericidal effect on some enterobacteria, yet could induce resistance in *Escherichia coli*. These resistances were associated with various modifications in the thymidine kinase gene.

Furthermore, an additive or synergistic activity between AZT and the two aminoglycoside antibiotics amikacin and gentamicin was observed against enterobacteria.

Accordingly, in one embodiment of the present invention there is provided the use of a combination of zidovudine and an anti-microbial polymyxin selected from colistin and polymyxin B, for treating a microbial infection.

In a further embodiment of the invention there is provided a pharmaceutical composition comprising zidovudine and a peptide such as a polymyxin selected from colistin and polymyxin B, and a pharmaceutically acceptable carrier for use in treating a microbial infection, preferably killing clinically latent microorganisms associated with a microbial infection.

The present invention is also based upon the unexpected finding that the activity of the combinations described herein is substantially improved compared to when either are administered alone. Moreover, the combinations have surprisingly been shown to exhibit synergistic antimicrobial activity against log phase (i.e. multiplying) and/or clinically latent microorganisms. The surprising biological activity of the combinations of the present invention offers the opportunity to shorten chemotherapy regimes and may result in a reduction in the emergence of microbial resistance associated with the use of such combinations.

In another embodiment, the invention provides the use of zidovudine and and a polymyxin selected from colistin and polymyxin B, or a pharmaceutically acceptable salt thereof for the manufacture of a medicament for treating a microbial infection, preferably killing clinically latent microorganisms associated with a microbial infection.

In a further embodiment, the invention provides a method of treating a microbial infection, preferably killing clinically latent microorganisms associated with a microbial infection which comprises administering to a mammal, including man, zidovudine and a polymyxin selected from colistin and polymyxin B, or a pharmaceutically acceptable salt thereof in combination.

As used herein, the term "in combination with" covers both separate and sequential administration of the anti-retroviral agent and antimicrobial agent. For example, when the agents are administered sequentially, either the zidovudine or pepide may be administered first. When administration is simultaneous, the agents may be administered either in the same or a different pharmaceutical composition. Adjunctive therapy, i.e. where one agent is used as a primary treatment and the other agent is used to assist that primary treatment, is also an embodiment of the present invention.

According to a further embodiment of the invention, there is provided a product comprising zidovudine and a polymyxin selected from colistin and polymyxin B, as a combined preparation for simultaneous, separate or sequential use in treating microbial infections particularly by killing clinically latent microorganisms associated with a microbial infection.

There is also provided a pharmaceutical composition comprising zidovudine and a polymyxin selected from colistin and polymyxin B, and a pharmaceutically acceptable adjuvant, diluent or carrier. Such a composition may be used for the treatment of microbial infections, in particular for killing clinically latent microorganisms associated with such infections.

The combinations of the present invention may be used to treat microbial infections. In particular they may be used to kill multiplying and/or clinically latent microorganisms associated with microbial infections. References herein to the treatment of a microbial infection therefore include killing multiplying and/or clinically latent microorganisms associated with such infections. Preferably, the combinations of the present invention are used to kill clinically latent microorganisms associated with microbial infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection. Preferably, the term "microbial" in these contexts, means "bacterial."

As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

Streptococci (e.g.beta-haemolytic, pyogenic streptococci (such as *Strept. agalactiae, Strept. canis, Strept. dysgalactiae dysgalactiae, Strept. dysgalactiae equisimilis, Strept. equi equi, Strept. equi zooepidemicus, Strept. iniae, Strept. porcinus* and *Strept. pyogenes*), microaerophilic, pyogenic streptococci (*Streptococcus* "milleri", such as *Strept. anginosus, Strept. constellatus constellatus, Strept. constellatus pharyngidis* and *Strept. intermedius*), oral streptococci of the "mitis" (alpha-haemolytic—*Streptococcus* "viridans", such as *Strept. mitis, Strept. oralis, Strept. sanguinis, Strept. cristatus, Strept. gordonii* and *Strept. parasanguinis*), "salivarius" (non-haemolytic, such as *Strept. salivarius* and *Strept. vestibularis*) and "mutans" (tooth-surface streptococci, such as *Strept. criceti, Strept. mutans, Strept. ratti* and *Strept. sobrinus*) groups, *Strept. acidominimus, Strept. bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri;*

Bacillaceae, such as *Bacillus anthracis, Bacillus subtilis, Bacillus thuringiensis, Bacillus stearothermophilus* and *Bacillus cereus;*

Enterobacteriaceae, such as *Escherichia coli, Enterobacter* (e.g. *Enterobacter aerogenes, Enterobacter agglomerans* and *Enterobacter cloacae*), Citrobacter (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

*Helicobacter* (e.g. *Helicobacter pylori, Helicobacter cinaedi* and *Helicobacter fennelliae*);

Acinetobacter (e.g. *A. baumanii, A. calcoaceticus, A. haemolyticus, A. johnsonii, A. junii, A. Iwoffi* and *A. radioresistens*);

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*);

*Bacteriodes fragilis;*

*Peptococcus* (e.g. *Peptococcus niger*);

Peptostreptococcus;

Clostridium (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);

Mycoplasma (e.g. *M. pneumoniae, M. hominis, M. genitalium* and *M. urealyticum*);

Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*); *Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);

*Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*);

*Actinomyces* (e.g. *Actinomyces israelii*);

*Brucella* (e.g. *Brucella abortus, Brucella canis, Brucella melintensis* and *Brucella suis*);

*Campylobacter* (e.g. *Campylobacter jejuni, Campylobacter coli, Campylobacter lari* and *Campylobacter fetus*);

*Listeria monocytogenes;*

*Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae;*

Corynebacteriaceae (e.g. *Corynebacterium diphtheriae, Corynebacterium jeikeum* and *Corynebacterium urealyticum*);

Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*); *Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

*Bordetella* (e.g. *Bordetella bronchiseptica, Bordetella hinzii, Bordetella holmseii, Bordetella parapertussis, Bordetella pertussis* and *Bordetella trematum*);

Nocardiaceae, such as *Nocardia* (e.g. *Nocardia asteroides* and *Nocardia brasiliensis*);

Rickettsia (e.g. *Ricksettsii* or *Coxiella burnetii*);

*Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis* and

*Legionalla wadsworthii*);

*Moraxella catarrhalis;*

*Cyclospora cayetanensis;*

*Entamoeba histolytica;*

*Giardia lamblia;*

*Trichomonas vaginalis;*

*Toxoplasma gondii;*

*Stenotrophomonas maltophilia;*

*Burkholderia cepacia; Burkholderia mallei* and *Burkholderia pseudomallei;*

*Francisella tularensis;*

*Gardnerella* (e.g. *Gardneralla vaginalis* and *Gardneralla mobiluncus*); *Streptobacillus moniliformis;*

Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

*Bartonella* (*Bartonella bacilliformis, Bartonella clarridgeiae, Bartonella elizabethae, Bartonella henselae, Bartonella quintana* and *Bartonella vinsonii arupensis*);

*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

*Spirillium* (e.g. *Spirillum minus*);

*Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

*Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*); *Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);

*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

*Chlamydia* (e.g. *Chlamydia trachomatis*);

*Cryptosporidium* (e.g. *C. parvum, C. hominis, C. canis, C. felis, C. meleagridis* and *C. muris*);

*Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));

*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);

*Gemella* (e.g. *Gemella bergeri, Gemella haemolysans, Gemella morbillorum* and *Gemella sanguinis*); and

*Ureaplasma* (e.g. *Ureaplasma parvum* and *Ureaplasma urealyticum*).

Particular bacteria that may be treated using a combination of the invention include:

Gram positive bacteria;

Staphylococci, such as *Staph. aureus* (either Methicillin-sensitive (i.e. MSSA) or Methicillin-resistant (i.e. MRSA)) and *Staph. epidermidis;*

Streptococci, such as *Strept. agalactiae* and *Strept. pyogenes;*

Bacillaceae, such as *Bacillus anthracis;*

Enterococci, such as *Enterococcus faecalis* and *Enterococcus faecium*; and

Gram negative bacteria;

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*);

*Haemophilis influenzae;*

Mycobacteria, such as *Mycobacterium tuberculosis.*

Preferably, the bacterial infections treated by the combinations described herein are gram-negative infections.

Preferably, the bacterium is Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*). The combination of the present invention is particularly beneficial in treating (multi)-drug-resistant ((M)DR) bacteria. With respect to Enterobacteriaceae, drug resistance most often builds up to carbapenemase i.e. carbapenemase-resistant strains and "extended spectrum β-lactamase" (ESBL) strains for example New Delhi Metallo-beta-lactamase-1 (NDM-1) resistant *Klebs. Pneumonia*. Most preferably, the microbial infection treated is an infection caused by one or more of *E. coli, Klebsiella pneumoniae* or one of the KES (*Klebsiella, Enterobacter* and *Serratia*) group bacteria. In all embodiments it is preferable that the combination therapy is synergistic as compared to the administration of the combination components taken alone.

It should be kept in mind that although a combination such as that claimed may initially be demonstrated to be functional in treating (M)DR strains, they can then be used in treating non-resistant strains. This is especially valuable in the context of the presently claimed combination where the primary therapy for Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*) are anti-microbial drugs that are expensive due to prevailing patent protection. The replacement of such "ethical" drugs by a combination of "generic" antibiotics is thought to be beneficial from a therapeutic perspective as well as financial/economic perspective in times where governments are seeking to reduce the cost of healthcare.

The combinations of the present invention may be used to treat infections associated with any of the above-mentioned bacterial organisms, and in particular they may be used for killing multiplying and/or clinically latent microorganisms associated with such an infection. In one aspect the invention provides the use of zidovudine in combination with polymyxin B or colistin, preferably colistin, for treating microbial infections, particularly for killing clinically latent microorganisms associated with a microbial infection.

Particular conditions which may be treated using the combination of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, gardnerella vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea capitis, tinea cruris, tinea pedis and tinea unguium), onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* and *Enterococcus faecium.*

It will be appreciated that references herein to "treatment" extend to prophylaxis as well as the treatment of established diseases or symptoms.

Compounds for use according to the invention may be administered as the raw material but the active ingredients are preferably provided in the form of pharmaceutical compositions.

The active ingredients may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient.

Preferably, the compositions of the invention are formulated for oral or topical administration. In a preferred embodiment, the composition is a cream or an ointment adapted for nasal administration, in particular for delivery to the anterior nares.

The formulations may conveniently be presented in unit dosage form and may be prepared by any of the methods well known in the art of pharmacy e.g. as described in "*Remington: The Science and Practice of Pharmacy*", Lippincott Williams and Wilkins, 21st Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the Staphylococci, Streptococci, *Mycobacteria* or *Pseudomonas* organisms mentioned hereinbefore, such as *S. aureus* (e.g. Methicillin resistant *S. aureus* (MRSA))).

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndr ome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellulare, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczma, burns, abrasions and skin wounds.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combination of the invention by means of a single patient pack, or patient packs of each composition, including a package insert directing the patient to the correct use of the invention is a desirable feature of this invention.

According to a further embodiment of the present invention there is provided a patient pack comprising at least one active ingredient of the combination according to the invention and an information insert containing directions on the use of the combination of the invention.

Suitable dosages and formulations for the administration of colistin are described in the product label for Colomycin® which can be found at http://www.medicines.orq.uk/emc/medicine/6301/SPC/Colomvcin+Tablets/

Suitable dosages and formulations for the administration of zidovudine are described in the product label for Retrovir® oral solution or capsules which can be found at http://www.medicines.org.uk/emdmedicine/12444/SPC/Retrovir+250mg+Capsules/

The route of administration and dosage of polymyxin B is generally determined by the administering physician. Typically, polymyxin B is administered by topical, intramuscular, intravenous, intrathecal or ophthalmic routes depending on the nature of the bacterial infection.

The administration of the combination of the invention by means of a single patient pack, or patient packs of each composition, including a package insert directing the patient to the correct use of the invention is a desirable feature of this invention.

According to a further embodiment of the present invention there is provided a patient pack comprising at least one active ingredient of the combination according to the invention and an information insert containing directions on the use of the combination of the invention.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-doses per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:

(1) growing a bacterial culture to stationery phase;

(2) treating the stationery phase culture with one or more antimicrobial agents at a concentration and or time sufficient to kill growing bacteria, thereby selecting a phenotypically resistant sub-population;

(3) incubating a sample of the phenotypically resistant subpopulation with one or more test compounds or agents; and (4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

EXAMPLES

Example 1

In Vitro Activity of Zidovudine Combined Together with Colistin Against Log Phase *Escherichia coli* and *Klebsiella pneumoniae* Using Chequerboard Method Compounds and Preparation HT0120663: Zidovudine HT0120663; MIC before combination was 4 μg/ml and decreased to 1 μg/ml if combined with 2 μg/ml of colistin.

Colistin: MIC for colistin before combination was 4 μg/ml and reduced to 0.25 μg/ml when combined with 2 μg/ml of HT0120663.

The FIC index is 0.156 indicating a synergistic combination.

Using the techniques described above, combinations of HT0120663 with colistin were determined by chequerboard analysis against 91 Gram negative antibiotic-resistant bacteria including NDM-1 strains. The bacteria were all selected from; are *E. coli, Klebsiella pneumoniae* and KES (*Klebsiella, Enterobacter* and *Serratia*) group bacteria. The overall results are shown in the Table;

| Combination activities | FICI | HT0120663/colistin No of G- antibiotic resistant bacteria including NDM-1 |
|---|---|---|
| synergy | ≤0.5 | 26 |
| no interaction | >0.5 < 4 | 65 |
| antagonism | >4 | 0 |

HT0120663 in combination with colistin has been tested against 91 Gram negative antibiotic-resistant clinical isolates including 7 NDM-1 strains using chequerboard method. Synergistic activity was seen in 26 strains and no interaction of the combination was shown in 65 strains. No antagonism was observed.

Example 2

FIG. 1 shows HT0120663 in combination with Colistin against log phase *Klebsiella* using time kill curve.

HT0120663 at 4 μg/ml showed about 1 log kill at 6 hours followed by regrowth of the bacteria. Colistin at 16 μg/ml showed inhibition up to 6 hours. However, HT0120663 in combination with colistin increased bactericidal activity of both drugs and completely removed $10^7$ bacteria at 24 hours showing a significant synergistic activity.

The invention claimed is:

1. A method of killing multiplying bacteria associated with a gram-negative bacterial infection which comprises administering to a mammal having said gram-negative bacterial infection a combination of zidovudine and a polymyxin selected from colistin and polymyxin B, or a pharmaceutically acceptable salt thereof, wherein the combination exhibits synergistic antibacterial activity against the multiplying bacteria caused by *Escherichia coli, Klebsiella*, or *Enterobacter.*

2. The method according to claim 1, wherein the polymyxin is colistin or a pharmaceutically acceptable salt thereof.

3. A pharmaceutical composition comprising zidovudine in combination with a polymyxin selected from colistin and polymyxin B; and a pharmaceutically acceptable salt thereof; and a pharmaceutically acceptable adjuvant, diluent or carrier, wherein the combination exhibits synergistic antibacterial activity against multiplying bacteria associated with a gram-negative bacterial infection caused by *Escherichia coli, Klebsiella*, or *Enterobacter.*

4. The pharmaceutical composition according to claim 3, wherein the polymyxin is colistin.

5. The pharmaceutical composition according to claim 3 which is formulated for oral or topical administration.

6. The method according to claim 1 wherein the bacterial infection is caused by drug-resistant bacteria.

* * * * *